United States Patent
Ito et al.

(10) Patent No.: US 11,808,717 B2
(45) Date of Patent: Nov. 7, 2023

(54) X-RAY TUBE BILLING SYSTEM

(71) Applicant: Shimadzu Corporation, Kyoto (JP)

(72) Inventors: Fumihiko Ito, Kyoto (JP); Yuji Maeda, Kyoto (JP); Taketo Kishi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 361 days.

(21) Appl. No.: 17/421,873

(22) PCT Filed: Dec. 19, 2019

(86) PCT No.: PCT/JP2019/049825
§ 371 (c)(1),
(2) Date: Jul. 9, 2021

(87) PCT Pub. No.: WO2020/166203
PCT Pub. Date: Aug. 20, 2020

(65) Prior Publication Data
US 2022/0107278 A1    Apr. 7, 2022

(30) Foreign Application Priority Data
Feb. 13, 2019 (JP) ................. 2019-023865

(51) Int. Cl.
*G01N 23/04* (2018.01)
*G06Q 20/14* (2012.01)
*A61B 6/00* (2006.01)

(52) U.S. Cl.
CPC .......... *G01N 23/043* (2013.01); *A61B 6/487* (2013.01); *G06Q 20/145* (2013.01)

(58) Field of Classification Search
CPC ..... G01N 23/043; A61B 6/487; G06Q 20/145
See application file for complete search history.

(56) References Cited

U.S. PATENT DOCUMENTS

2005/0197864 A1    9/2005    Koritzinsky et al.
2007/0179817 A1*   8/2007    Sauer ................. G06F 21/10
                                                              705/4
(Continued)

FOREIGN PATENT DOCUMENTS

JP    2004-046489 A    2/2004
JP    2004-097634 A    4/2004
(Continued)

OTHER PUBLICATIONS

Office Action dated Feb. 7, 2023, in corresponding Japanese Application No. 2022-077218, 14 pages.
(Continued)

*Primary Examiner* — Chih-Cheng Kao
(74) *Attorney, Agent, or Firm* — Maier & Maier, PLLC

(57) ABSTRACT

An X-ray tube billing system for a fluoroscopic apparatus for non-destructive inspection configured to perform X-ray fluoroscopy on a subject using an X-ray tube includes a fluoroscopy time detector configured to detect a length of time during which the X-ray fluoroscopy has been performed using the X-ray tube, and a billing amount calculator configured to calculate a billing amount related to use of the X-ray tube based on the length of time during which the X-ray fluoroscopy has been performed, which is detected by the fluoroscopy time detector.

19 Claims, 8 Drawing Sheets

(56) References Cited

U.S. PATENT DOCUMENTS

| | | | |
|---|---|---|---|
| 2008/0201166 A1* | 8/2008 | Warner | G06Q 30/04 705/2 |
| 2011/0013220 A1 | 1/2011 | Sabol et al. | |
| 2012/0290312 A1* | 11/2012 | Maruoka | G06Q 30/0283 705/30 |
| 2014/0324477 A1 | 10/2014 | Oez | |

FOREIGN PATENT DOCUMENTS

| | | |
|---|---|---|
| JP | 2011-019905 A | 2/2011 |
| JP | 2013-152506 A | 8/2013 |
| KR | 10-2011-0051489 A | 5/2011 |

OTHER PUBLICATIONS

International Search Report (with English translation) and Written Opinion (with Machine translation) dated Mar. 10, 2020 in corresponding International Application No. PCT/JP2019/049825; 14 pages.

" '利用料金について 微細構造解析プラ ットフォーム共用設備運用サイト [online]" (Regarding usage fees, microstructure analysis platform shared facility operation site [online]), Institute of Engineering Innovation, School of Engineering, the University of Tokyo; Aug. 5, 2018 Retrieved Feb. 2020; URL:https://web.archive.org/web/20180805145125/http://lcnet.t.u-tokyo.ac.jp/fee.php Machine translation attached.

Office Action dated Dec. 7, 2021 in Japanese Patent Application No. 2020-572109 with Computer Generated English translation; 10 pgs.

Office Action dated Aug. 1, 2023, in corresponding Japanese Application No. 2022-077218, 11 pages.

Decision of Refusal dated Mar. 1, 2022 in corresponding Japanese Application No. 2020-572109; 8 pages including English-language translation.

* cited by examiner

X-RAY TUBE BILLING SYSTEM

FIELD

The present invention relates to an X-ray tube billing system.

BACKGROUND

Conventionally, a billing system for an X-ray imaging apparatus is known (see Patent Document 1, for example).

Patent Document 1 discloses a management system (billing system) for a medical digital X-ray imaging apparatus. In this management system, the medical digital X-ray imaging apparatus adds an imaging counter along with image capturing and transmits imaging counter information to a server apparatus. The server apparatus performs billing calculation according to the received imaging counter information.

PATENT DOCUMENT

Patent Document 1: Japanese Patent Laid-Open No. 2004-097634

SUMMARY

As described above, the management system described in Patent Document 1 charges based on the number of imaging counters (i.e., the number of times of X-ray imaging). However, in a fluoroscopic apparatus, the time taken for one-time X-ray imaging (X-ray fluoroscopy) differs depending on a user. Therefore, there is a problem that it is not possible to charge fairly only by charging based on the number of times of X-ray imaging. Note that X-ray fluoroscopy refers to moving image capturing in which a subject is continuously imaged with a smaller X-ray dose as compared with normal X-ray imaging.

The present invention is intended to solve the above problem. The present invention aims to provide an X-ray tube billing system capable of charging fairly even when the time taken for one-time X-ray fluoroscopy differs depending on a user when a fluoroscopic apparatus is used.

Means for Solving the Problem

In order to attain the aforementioned object, an X-ray tube billing system for a fluoroscopic apparatus for non-destructive inspection configured to perform X-ray fluoroscopy on a subject using an X-ray tube according to an aspect of the present invention includes a fluoroscopy time detector configured to detect a length of time during which the X-ray fluoroscopy has been performed using the X-ray tube, and a billing amount calculator configured to calculate a billing amount related to use of the X-ray tube based on the length of time during which the X-ray fluoroscopy has been performed, which is detected by the fluoroscopy time detector.

According to the present invention, as described above, the billing amount calculator is provided to calculate the billing amount related to the use of the X-ray tube based on the length of time during which X-ray fluoroscopy has been performed, which is detected by the fluoroscopy time detector. Thus, it is possible to charge based on the length of time during which X-ray fluoroscopy has been performed, and thus it is possible to provide the X-ray tube billing system capable of charging fairly even when the time taken for one-time X-ray fluoroscopy differs depending on the user unlike a case of charging based on the number of times of X-ray fluoroscopy when the fluoroscopic apparatus for non-destructive inspection is used.

DETAILED DESCRIPTION

Embodiments embodying the present invention are hereinafter described on the basis of the drawings.

First Embodiment

The configuration of an X-ray tube billing system 100 according to a first embodiment of the present invention is now described with reference to FIGS. 1 to 9.

Configuration of X-Ray Tube Billing System

Figure 1:
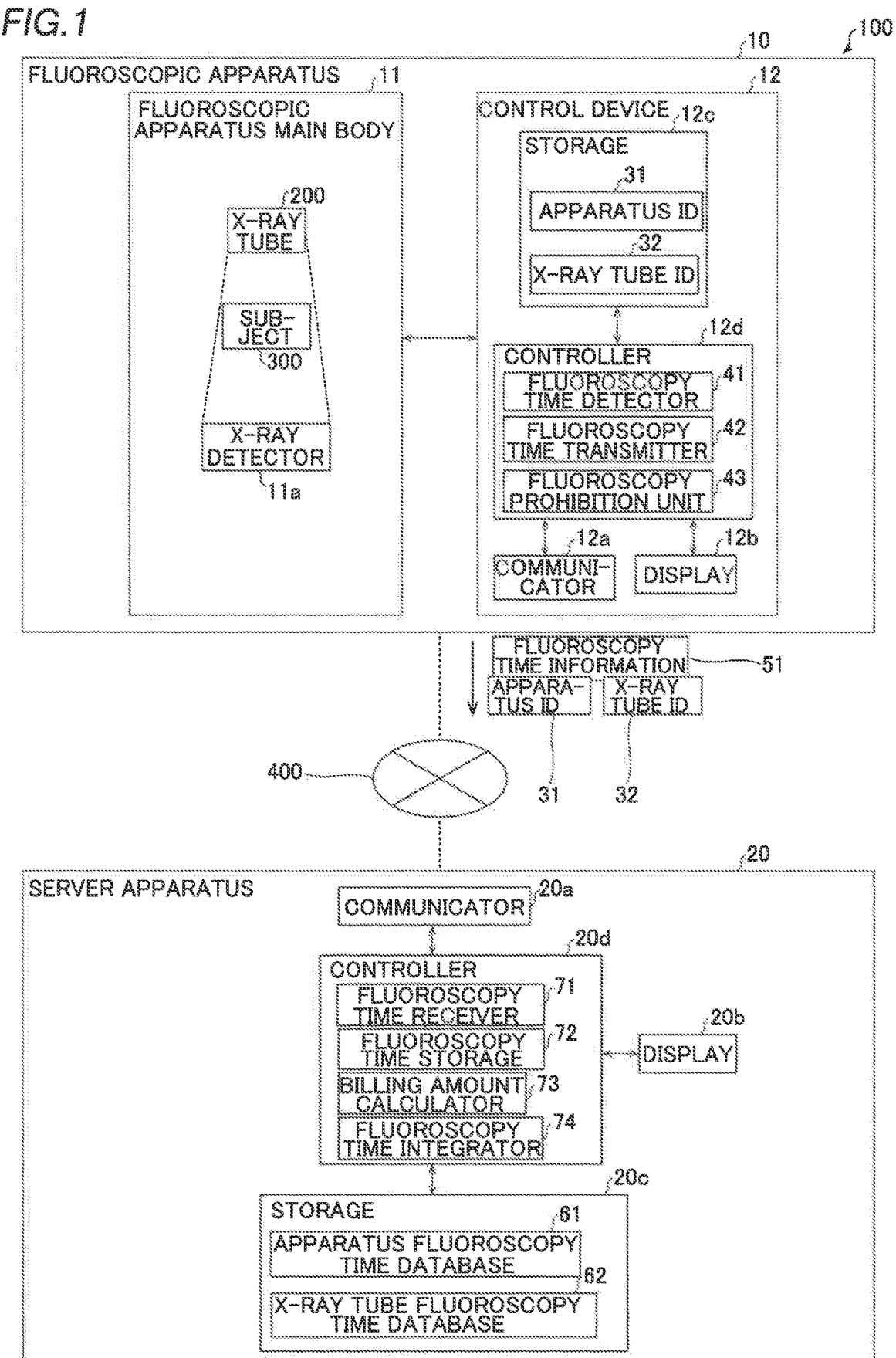
FIG. 1 is a schematic view showing the overall configuration of an X-ray tube billing system according to a first embodiment of the present invention.

As shown in FIG. 1, the X-ray tube billing system 100 is an X-ray tube billing system (management system) for a fluoroscopic apparatus 10 for non-destructive inspection that performs X-ray fluoroscopy on a subject 300 using an X-ray tube 200. The X-ray tube 200 lent from a lender is attached to the fluoroscopic apparatus 10. The X-ray tube billing system 100 is configured to calculate a billing amount related to the use of the X-ray tube 200, which is a rental item in the fluoroscopic apparatus 10.

The X-ray tube billing system 100 includes the fluoroscopic apparatus 10 and a server apparatus 20. The fluoroscopic apparatus 10 is an apparatus that performs X-ray fluoroscopy on the inanimate subject 300. Note that X-ray fluoroscopy refers to a moving image capturing in which the subject 300 is continuously imaged with a smaller X-ray dose as compared with normal X-ray imaging. The subject 300 may be a circuit board, an electronic component, or the like, for example. The fluoroscopic apparatus 10 can perform a non-destructive inspection on the subject 300 by imaging the inside of the subject 300 by X-ray fluoroscopy.

The fluoroscopic apparatus 10 includes a fluoroscopic apparatus main body 11 and a control device 12. The fluoroscopic apparatus main body 11 includes the X-ray tube 200, which is a rental item, and an X-ray detector 11a. The X-ray tube 200 is an electron tube that generates X-rays. The X-rays generated by the X-ray tube 200 are radiated to the subject 300 when the subject 300 is imaged. The X-ray detector 11a detects X-rays radiated from the X-ray tube 200 and transmitted through the subject 300. Furthermore, the X-ray detector 11a transmits electric signals according to the detected X-rays. The inside of the subject 300 is imaged based on the electric signals transmitted from the X-ray detector 11a. The X-ray detector 11a includes a flat panel detector (FPD) that is a detector for X-rays, for example.

The control device 12 is a personal computer communicably connected to the fluoroscopic apparatus main body 11, for example. The control device 12 includes a communicator 12a, a display 12b, a storage 12c, and a controller 12d. The communicator 12a is an interface for communication. The communicator 12a connects the fluoroscopic apparatus 10 to a network 400 such that the fluoroscopic apparatus 10 can communicate with the network 400. That is, the communicator 12a connects the fluoroscopic apparatus 10 to the server apparatus 20, which is a communication target connected to the network 400, such that the fluoroscopic apparatus 10 can communicate with the server apparatus 20 via the network 400. The network 400 is the Internet, for example. The display 12b is a liquid crystal monitor, for example, and displays information.

The storage 12c is a storage medium such as a flash memory, and stores information. The storage 12c stores an apparatus ID 31, which is identification information of the fluoroscopic apparatus 10, and an X-ray tube ID 32, which is identification information of the X-ray tube 200. The apparatus ID 31 may be the serial number of the fluoroscopic apparatus 10 attached to the fluoroscopic apparatus 10 at the time of manufacture, for example. Similarly, the X-ray tube ID 32 may be the serial number of the X-ray tube 200 attached to the X-ray tube 200 at the time of manufacture.

The controller 12d is a control circuit including a processor such as a CPU and a memory for storing information, for example. The controller 12d functions as a fluoroscopy time detector 41, a fluoroscopy time transmitter 42, and a fluoroscopy prohibition unit 43 by executing various programs (software). That is, in FIG. 1, the fluoroscopy time detector 41, the fluoroscopy time transmitter 42, and the fluoroscopy prohibition unit 43 are illustrated as software functional blocks. Note that the fluoroscopy time detector 41, the fluoroscopy time transmitter 42, and the fluoroscopy prohibition unit 43 are not limited to these, but the fluoroscopy time detector 41, the fluoroscopy time transmitter 42, and the fluoroscopy prohibition unit 43 may be configured in whole or in part by dedicated hardware circuits.

The controller 12d as the fluoroscopy time detector 41 performs a control to detect the length of time during which the fluoroscopic apparatus 10 has performed X-ray fluoroscopy on the subject 300 by the X-ray tube 200. The length of time during which X-ray fluoroscopy has been performed may be detected in any manner, and a timer may count the time from the time when a user operates an "X-ray fluoroscopy start button" until the time when the user operates an "X-ray fluoroscopy end button" to detect the length of time during which X-ray fluoroscopy has been performed, for example. Alternatively, the timer may count the time from the time when the tube voltage of the X-ray tube 200 becomes equal to or higher than a predetermined value until the time when the tube voltage becomes equal to or lower than a predetermined value to detect the length of time during which X-ray fluoroscopy has been performed.

The controller 12d as the fluoroscopy time transmitter 42 performs a control to transmit fluoroscopy time information 51, which is information on the length of time during which X-ray fluoroscopy has been performed, including information of the length of time during which X-ray fluoroscopy has been performed to the server apparatus 20 via the network 400 by the communicator 12a. Specifically, the controller 12d as the fluoroscopy time transmitter 42 performs a control to transmit, to the server apparatus 20 via the network 400 by the communicator 12a, the fluoroscopy time information 51 in association with the apparatus ID 31 and the X-ray tube ID 32 stored in the storage 12c. The fluoroscopy time information 51 may be transmitted at any timing, and the fluoroscopy time information 51 may be transmitted every time X-ray fluoroscopy is completed, for example. In this case, the fluoroscopy time information 51 includes information of the length of time during which X-ray fluoroscopy has been performed once. Alternatively, the fluoroscopy time information 51 may be transmitted periodically. In this case, the fluoroscopy time information 51 may include information of the length of time during which X-ray fluoroscopy has been performed a plurality of times. The operation of the controller 12d as the fluoroscopy prohibition unit 43 is described below.

The server apparatus 20 is a computer for calculating and managing the billing amount related to the use of the X-ray tube 200. The server apparatus 20 includes a communicator 20a, a display 20b, a storage 20c, and a controller 20d. The communicator 20a is an interface for communication. The communicator 20a connects the server apparatus 20 to the network 400 such that the server apparatus 20 can communicate with the network 400. That is, the communicator 20a connects the server apparatus 20 to the fluoroscopic apparatus 10, which is a communication target connected to the network 400, such that the server apparatus 20 can communicate with the fluoroscopic apparatus 10 via the network 400. FIG. 1 shows only one fluoroscopic apparatus 10 connected to the server apparatus 20 for ease of understanding, but actually, more than one fluoroscopic apparatus 10 may be connected to the server apparatus 20. That is, the server apparatus 20 may be connected to the fluoroscopic apparatuses 10 of a plurality of customers (users), and the billing amount for each of the plurality of customers may be calculated and managed.

Figure 2:
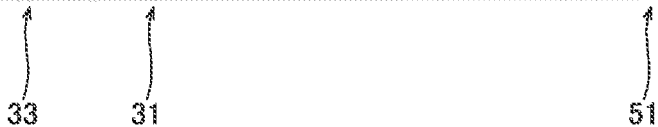
FIG. 2 is a schematic view illustrating apparatus fluoroscopy time database of a server apparatus according to the first embodiment of the present invention.
Figure 3:
FIG. 3 is a schematic view illustrating X-ray tube fluoroscopy time database of the server apparatus according to the first embodiment of the present invention.

The display 20b is a liquid crystal monitor, for example, and displays information. The storage 20c is a large-capacity storage medium such as a hard disk drive, and stores information. The storage 20c stores apparatus fluoroscopy time database 61 and X-ray tube fluoroscopy time database 62. As shown in FIG. 2, in the apparatus fluoroscopy time database 61, the fluoroscopy time information 51 transmitted from the fluoroscopic apparatus 10 is stored separately for each apparatus ID 31. The apparatus ID 31 is associated with a customer ID 33, which is identification information of a customer (user). That is, in the apparatus fluoroscopy time database 61, the fluoroscopy time information 51 transmitted from the fluoroscopic apparatus 10 is stored separately for each customer ID 33. As shown in FIG. 3, in the X-ray tube fluoroscopy time database 62, the fluoroscopy time information 51 transmitted from the fluoroscopic apparatus 10 is stored separately for each X-ray tube ID 32.

As shown in FIG. 1, the controller 20d is a control circuit that includes a processor such as a CPU and a memory for storing information, for example, and controls the operation of each portion of the server apparatus 20. The controller 20d functions as a fluoroscopy time receiver 71, a fluoroscopy time storage 72, a billing amount calculator 73, and a fluoroscopy time integrator 74 by executing various programs (software). That is, in FIG. 1, the fluoroscopy time receiver 71, the fluoroscopy time storage 72, the billing amount calculator 73, and the fluoroscopy time integrator 74 are illustrated as software functional blocks. Note that the fluoroscopy time receiver 71, the fluoroscopy time storage 72, the billing amount calculator 73, and the fluoroscopy time integrator 74 are not limited to these, but the fluoroscopy time receiver 71, the fluoroscopy time storage 72, the billing amount calculator 73, and the fluoroscopy time integrator 74 may be configured in whole or in part by dedicated hardware circuits.

The controller 20d as the fluoroscopy time receiver 71 performs a control to receive the fluoroscopy time information 51, which is information on the length of time during which X-ray fluoroscopy has been performed, including the information of the length of time during which X-ray fluoroscopy has been performed from the fluoroscopic apparatus 10 via the network 400 by the communicator 20a. Specifically, the controller 20d as the fluoroscopy time receiver 71 performs a control to receive the fluoroscopy time information 51 associated with the apparatus ID 31 and the X-ray tube ID 32 from the fluoroscopic apparatus 10 via the network 400 by the communicator 20a.

The controller 20d as the fluoroscopy time storage 72 performs a control to store the received fluoroscopy time information 51 in the storage 20c. Specifically, the controller 20d as the fluoroscopy time storage 72 performs a control to store, in the apparatus fluoroscopy time database of the storage 20c, the received fluoroscopy time information 51 separately for each apparatus ID 31 based on the apparatus ID 31 associated with the fluoroscopy time information 51. Similarly, the controller 20d as the fluoroscopy time storage 72 performs a control to store, in the X-ray tube fluoroscopy time database 62 of the storage 20c, the received fluoroscopy time information 51 separately for each X-ray tube ID 32 based on the X-ray tube ID 32 associated with the fluoroscopy time information 51.

Figure 4:
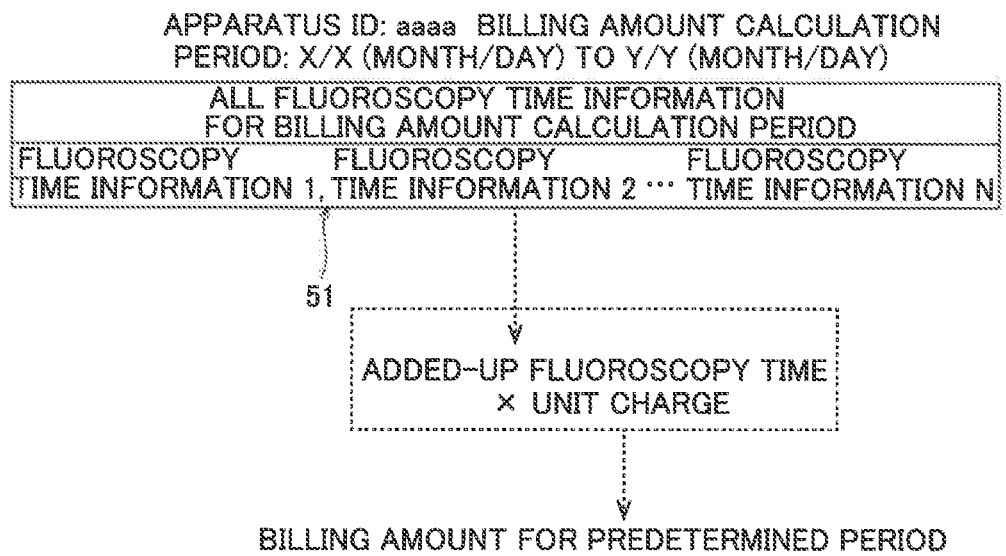
FIG. 4 is a schematic view illustrating calculation of the billing amount of the X-ray tube billing system according to the first embodiment of the present invention.

In the first embodiment, the controller 20d as the billing amount calculator 73 performs a control to acquire the length of time during which X-ray fluoroscopy has been performed by the X-ray tube 200 in the fluoroscopic apparatus 10 from the fluoroscopy time information 51. Then, as shown in FIG. 4, the controller 20d as the billing amount calculator 73 performs a control to calculate the billing amount (charge) related to the use of the X-ray tube 200 based on the acquired length of time during which X-ray fluoroscopy has been performed.

First, the controller 20d as the fluoroscopy time integrator 74 perform a control to add up the length of time during which X-ray fluoroscopy has been performed during a predetermined period that is a billing amount calculation period. The predetermined period may be any period, and may be one month, for example. In this case, the controller 20d as the fluoroscopy time integrator 74 performs a control to add up the length of time during which X-ray fluoroscopy has been performed on a monthly basis. That is, the length of time during which X-ray fluoroscopy has been performed during a billing month(s) of the billing amount, which is a month(s) from January to December that requires billing of the billing amount, may be added up.

At this time, the controller 20d as the fluoroscopy time integrator 74 performs a control to add up the time during which X-ray fluoroscopy has been performed during the predetermined period in association with the apparatus ID 31. That is, the controller 20d as the fluoroscopy time integrator performs a control to extract the fluoroscopy time information 51 corresponding to the predetermined period from the fluoroscopy time information 51 corresponding to the specific apparatus ID 31 stored in the apparatus fluoroscopy time database 61, and to add up the time during which X-ray fluoroscopy has been performed during the predetermined period based on the extracted fluoroscopy time information 51.

Then, the controller 20d as the billing amount calculator 73 calculates the billing amount of a specific fluoroscopic apparatus 10 (in FIG. 4, a fluoroscopic apparatus having an apparatus ID 31 "aaaa") for the predetermined period based on the added-up length of time during which X-ray fluoroscopy has been performed during the predetermined period. That is, the controller 20d as the billing amount calculator 73 calculates the billing amount of a specific user (in FIG. 4, a user whose customer ID 33 is "AAAA") for the predetermined period. The billing amount based on the length of time during which X-ray fluoroscopy has been performed may be calculated in any manner, and FIG. 4 shows an example in which the billing amount is calculated by multiplying the length of time during which X-ray fluoroscopy has been performed by a predetermined unit charge. A lower limit, an upper limit, or the like may be set for the billing amount.

For example, when the billing amount calculated based on the length of time during which X-ray fluoroscopy has been performed is equal to or less than the lower limit, a predetermined lower limit may be used as the billing amount charged to the user regardless of the calculated billing amount. That is, the controller 20d as the billing amount calculator 73 may be configured to set the lower limit as the billing amount when the billing amount calculated based on the length of time during which X-ray fluoroscopy has been performed is compared with the predetermined lower limit and the calculated billing amount is equal to or less than the lower limit. When the billing amount calculated based on the length of time during which X-ray fluoroscopy has been performed is equal to or more than the upper limit, a predetermined upper limit may be used as the billing amount charged to the user regardless of the calculated billing amount. That is, the controller 20d as the billing amount calculator 73 may be configured to set the upper limit as the billing amount when the billing amount calculated based on the length of time during which X-ray fluoroscopy has been performed is compared with the predetermined upper limit and the calculated billing amount is equal to or more than the upper limit. Thus, the controller 20*d* as the billing amount calculator 73 calculates the billing amount of the specific fluoroscopic apparatus 10 for the predetermined period based on the added-up length of time during which X-ray fluoroscopy has been performed during the predetermined period and a predetermined charge system.

Figure 5:
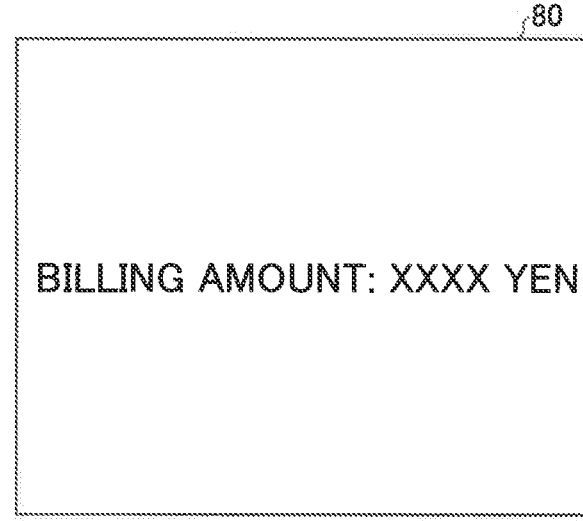
FIG. 5 is a schematic view illustrating calculation of the total usage time of an X-ray tube of the X-ray tube billing system according to the first embodiment of the present invention.

As shown in FIG. 5, the billing amount calculated by the controller 20*d* as the billing amount calculator 73 in the server apparatus 20 is displayed on a display 80 for the user to confirm the billing amount. The display 80 may be a display 12*b* of the fluoroscopic apparatus 10 used by the user who needs to confirm the billing amount or a display of a terminal (such as a personal computer or a mobile terminal) used by the user who needs to confirm the billing amount, for example. The controller 12*d* of the fluoroscopic apparatus 10 or a controller of the terminal owned by the user controls the display 80 (the display 12*b* or the display of the terminal) to display the billing amount calculated by the controller 20*d* as the billing amount calculator 73. The controller 12*d* of the fluoroscopic apparatus 10 or the controller of the terminal owned by the user is an example of a "display controller" in the claims.

The controller 20*d* as the billing amount calculator 73 may calculate the billing amount of the specific fluoroscopic apparatus 10 for the predetermined period based on the added-up length of time during which X-ray fluoroscopy has been performed during the predetermined period, using a different charge system for each apparatus ID 31 of the fluoroscopic apparatus 10. As an example, when the fluoroscopic apparatus 10 has an upper model and a general-purpose model, the upper model is preset to have a higher billing amount per hour than the lower model. Whether it is a higher model or a general-purpose model for each apparatus ID 31 is registered on the server apparatus 20 side such that the billing amount can be calculated with a different charge system for each apparatus ID 31. Similarly, the controller 20*d* as the billing amount calculator 73 may calculate the billing amount of the specific fluoroscopic apparatus 10 for the predetermined period based on the added-up length of time during which X-ray fluoroscopy has been performed during the predetermined period, using a different charge system for each X-ray tube ID 32. Similarly, both the apparatus ID 31 of the fluoroscopic apparatus 10 and the X-ray tube ID 32 may be used, and a charge system according to the combination of those IDs may be used.

The controller 12*d* as the fluoroscopy time transmitter 42 may be configured to transmit, to the server apparatus 20, the information (fluoroscopy time information 51) on the length of time during which X-ray fluoroscopy has been performed in association with a fluoroscopic mode used for the X-ray fluoroscopy. The controller 20*d* as the billing amount calculator 73 may calculate the billing amount of the specific fluoroscopic apparatus 10 for the predetermined period based on the added-up length of time during which X-ray fluoroscopy has been performed during the predetermined period, using a different charge system for each fluoroscopic mode. As an example, the fluoroscopic mode has a high image quality mode and a low image quality mode, and X-ray fluoroscopy may be performed using one fluoroscopic mode selected based on a user operation. It is conceivable that the high image quality mode places a greater burden on components (filaments, for example) of the X-ray tube 200 (the components are heavily consumed) and shortens the life of the X-ray tube 200. Therefore, the high image quality mode is preset to have a higher billing amount per hour than the low image quality mode. As another example, the fluoroscopic mode has a CT (three-dimensional) fluoroscopic mode and a two-dimensional fluoroscopic mode, and X-ray fluoroscopy may be performed using one fluoroscopic mode selected based on a user operation. Similarly, the controller 12*d* as the fluoroscopy time transmitter 42 may be configured to transmit, to the server apparatus 20, the information (fluoroscopy time information 51) on the length of time during which X-ray fluoroscopy has been performed in association with the fluoroscopic condition (the tube voltage (or the tube current; the same applies hereinafter)) used for X-ray fluoroscopy. The controller 20*d* as the billing amount calculator 73 may calculate the billing amount of the specific fluoroscopic apparatus 10 for the predetermined period based on the added-up length of time during which X-ray fluoroscopy has been performed during the predetermined period, using a different charge system for each tube voltage. It is conceivable that the higher tube voltage places a greater burden on the components (filaments, for example) of the X-ray tube 200 (the components are heavily consumed) and shortens the life of the X-ray tube. Therefore, the higher tube voltage is preset to have a higher billing amount per unit time than the lower tube voltage.

Alternatively, for each customer, a charge system for the customer may be determined based on the added-up length of fluoroscopy time during which X-ray fluoroscopy has been performed after replacement with a new X-ray tube 200 and before next replacement with a new X-ray tube 200 due to the life of the X-ray tube 200. For example, the charge system may be determined such that the longer added-up fluoroscopy time has a lower billing amount per unit time than the shorter added-up fluoroscopy time.

The information of the billing amount calculated by the controller 20*d* as the billing amount calculator 73 in the server apparatus 20 is transmitted from the server apparatus 20 to the device including the display 80 used by the user (such as the fluoroscopic apparatus 10 used by the user or the terminal used by the user) via the network 400. The information of the billing amount may be transmitted in any manner, and the information of the billing amount may be transmitted by e-mail or access to a website for checking the information of the billing amount, for example. Furthermore, the information of the billing amount that can be confirmed on the display 80 by the user may be information of the billing amount for the predetermined period, information of the billing amount in the middle of the predetermined period, information of the billing amount for the past predetermined period, or the like.

The billing amount calculated by the controller 20*d* as the billing amount calculator 73 in the server apparatus 20 may be displayed on the display 20*b* of the server apparatus 20. In this case, the controller 20*d* of the server apparatus 20 controls the display 20*b* to display the billing amount calculated by the controller 20*d* as the billing amount calculator 73. The controller 20*d* of the server apparatus 20 is an example of a "display controller" in the claims.

In the first embodiment, when the X-ray tube 200 is used after a long period of non-use, the life of the X-ray tube 200 may be shortened, and thus the controller 20*d* of the server apparatus 20 performs a control to confirm the usage of the X-ray tube 200 in the fluoroscopic apparatus 10 based on the fluoroscopy time information 51 (the information on the length of time during which X-ray fluoroscopy has been performed, which is associated with the X-ray tube ID 32) stored in the storage 20*c*. Specifically, the controller 20*d* performs a control to determine whether the X-ray tube 200 has not been used for a predetermined period in the fluoroscopic apparatus 10. When determining that the X-ray tube 200 has not been used for the predetermined period in the fluoroscopic apparatus 10, the controller 20d controls the communicator 20a to transmit, to the user using the fluoroscopic apparatus 10 via the network 400, information prompting the user to use the X-ray tube 200. Thus, it is possible to significantly reduce or prevent a shortening of the life of the X-ray tube 200 due to the use of the X-ray tube 200 after a long period of non-use.

Configuration of Calculation of Total Usage Time of X-Ray Tube

Figure 6:
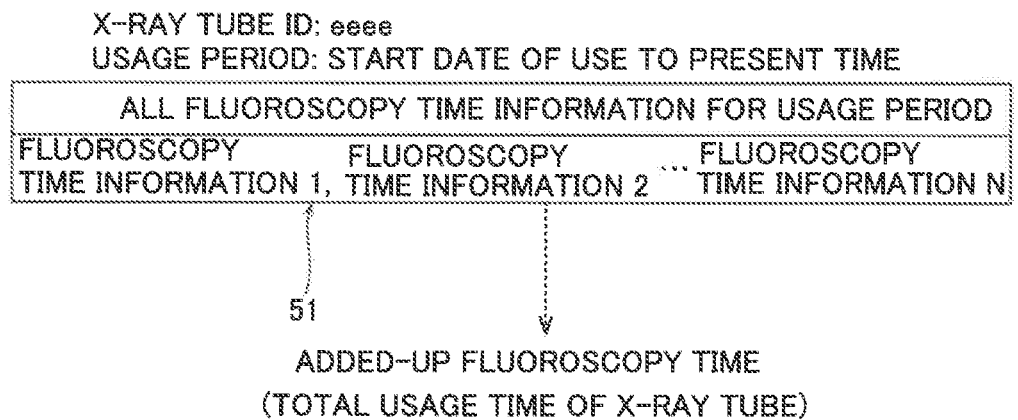
FIG. 6 is a schematic view illustrating display of the billing amount of the X-ray tube billing system according to the first embodiment of the present invention.

In the first embodiment, as shown in FIG. 6, the controller 20d as the fluoroscopy time integrator 74 performs a control to calculate the total usage time of the X-ray tube 200 from the start of use to the present time in addition to performing a control to calculate the billing amount of the fluoroscopic apparatus 10. The calculated total usage time of the X-ray tube 200 may be the total usage time in one fluoroscopic apparatus 10 or the total usage time in a plurality of fluoroscopic apparatuses 10. This is because the X-ray tube 200, which is a rental item, may be returned from a borrower and lent to the next borrower.

The controller 20d as the fluoroscopy time integrator 74 performs a control to add up the length of time during which X-ray fluoroscopy has been performed from the start of use of a specific X-ray tube 200 (in FIG. 6, an X-ray tube having an X-ray tube ID 32 "eeee") to the present time in association with the X-ray tube ID 32. That is, the controller 20d as the fluoroscopy time integrator 74 performs a control to add up the length of time during which X-ray fluoroscopy has been performed from the start of use of the specific X-ray tube 200 to the present time based on all fluoroscopy time information 51 corresponding to the specific X-ray tube ID 32 stored in the X-ray tube fluoroscopy time database 62.

The total usage time of the X-ray tube 200 calculated by the controller 20d as the fluoroscopy time integrator 74 is displayed on the display 20b of the server apparatus 20. The controller 20d controls the display 20b to display the total usage time of the X-ray tube 200 calculated by the controller 20d as the fluoroscopy time integrator 74 based on the operation of the server apparatus 20 by the user of the server apparatus 20.

Configuration of Prohibition of X-Ray Fluoroscopy by Fluoroscopic Apparatus

In the X-ray tube billing system 100 that calculates the billing amount and charges the user for the billing amount, it is a problem if the X-ray tube 200 can be used when the user's payment of the billing amount is delayed. Furthermore, when X-ray fluoroscopy is performed by the fluoroscopic apparatus 10, the fluoroscopy time information 51 is not accurately transmitted when the fluoroscopic apparatus 10 cannot transmit the fluoroscopy time information 51 to the server apparatus 20, and thus the billing amount cannot be accurately calculated.

Figure 7:
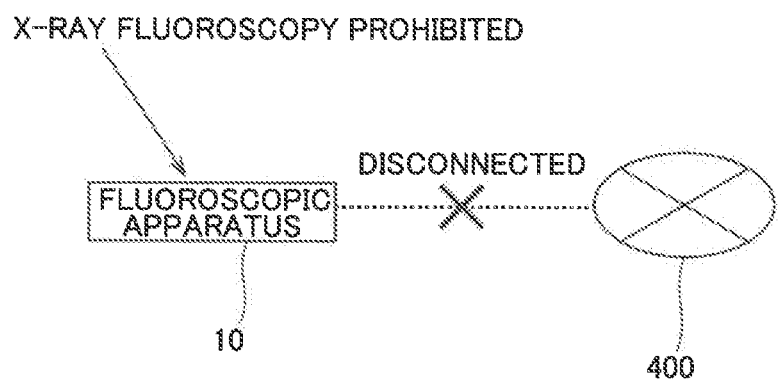
FIG. 7 is a schematic view illustrating a first example of prohibiting X-ray fluoroscopy of a fluoroscopic apparatus of the X-ray tube billing system according to the first embodiment of the present invention.
Figure 8:
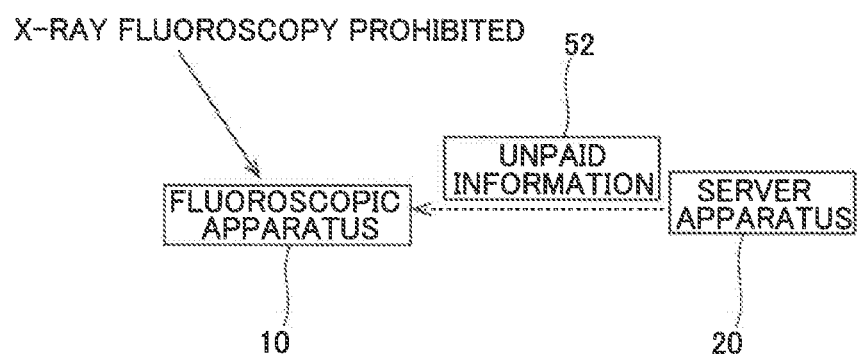
FIG. 8 is a schematic view illustrating a second example of prohibiting X-ray fluoroscopy of the fluoroscopic apparatus of the X-ray tube billing system according to the first embodiment of the present invention.

Therefore, in the first embodiment, as shown in FIGS. 7 and 8, the fluoroscopic apparatus 10 includes the controller 12d (see FIG. 1) as the fluoroscopy prohibition unit 43 that prohibits X-ray fluoroscopy in the situation described above.

As shown in FIG. 7, when X-ray fluoroscopy is performed by the fluoroscopic apparatus 10, the controller 12d as the fluoroscopy prohibition unit 43 performs a control to prohibit X-ray fluoroscopy by the fluoroscopic apparatus 10 when the controller 12d as the fluoroscopy time transmitter 42 cannot transmit the fluoroscopy time information 51. The control to prohibit X-ray fluoroscopy may be a control not to start X-ray fluoroscopy when an operation for starting X-ray fluoroscopy is received from the user, for example.

First, the controller 12d as the fluoroscopy prohibition unit 43 performs a control to determine whether the controller 12d as the fluoroscopy time transmitter 42 cannot transmit the fluoroscopy time information 51. For example, the controller 12d as the fluoroscopy prohibition unit 43 determines that the controller 12d as the fluoroscopy time transmitter 42 cannot transmit the fluoroscopy time information 51 when the fluoroscopic apparatus 10 is not connected to the network 400 via the communicator 12a.

Then, the controller 12d as the fluoroscopy prohibition unit 43 preforms a control to prohibit X-ray fluoroscopy by the fluoroscopic apparatus 10 when determining that the controller 12d as the fluoroscopy time transmitter 42 cannot transmit the fluoroscopy time information 51. Furthermore, the controller 12d as the fluoroscopy prohibition unit 43 performs a control to cancel prohibition of X-ray fluoroscopy by the fluoroscopic apparatus 10 when the controller 12d as the fluoroscopy time transmitter 42 transitions to a situation in which it can transmit the fluoroscopy time information 51 (when the fluoroscopic apparatus 10 is connected to the network 400, for example) while X-ray fluoroscopy by the fluoroscopic apparatus 10 is prohibited. That is, the controller 12d as the fluoroscopy prohibition unit 43 performs a control to allow X-ray fluoroscopy by the fluoroscopic apparatus 10.

As shown in FIG. 8, the controller 12d as the fluoroscopy prohibition unit 43 performs a control to prohibit X-ray fluoroscopy by the fluoroscopic apparatus 10 when the user's payment of the billing amount is not made by the date of payment, which is the payment due date.

Figure 9:
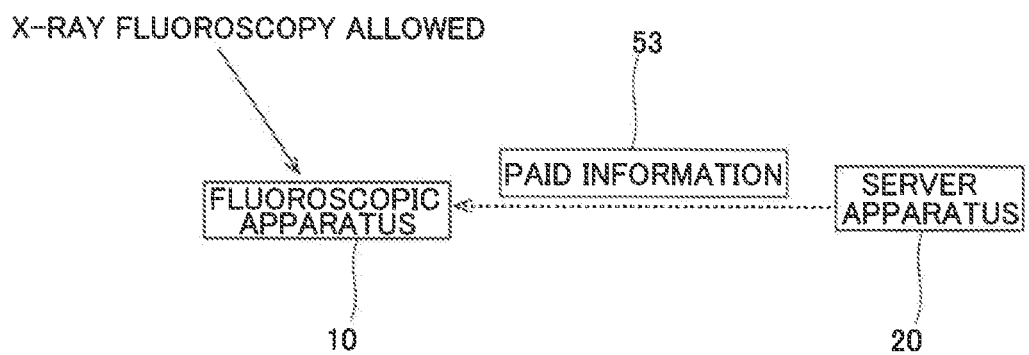
FIG. 9 is a schematic view illustrating transmission of paid information of the X-ray tube billing system according to the first embodiment of the present invention.

It is determined whether or not the user's payment of the billing amount has been made by the date of payment, which is the payment due date, based on payment information transmitted from the server apparatus 20. The server apparatus 20 manages information on whether or not the user's payment of the billing amount for the previous predetermined period has been made by the date of payment. As shown in FIGS. 8 and 9, the controller 20d of the server apparatus 20 performs a control to transmit unpaid information 52, which is information indicating that the user's payment is unpaid, to the fluoroscopic apparatus 10 when the user's payment is not made by the date of payment, and performs a control to transmit paid information 53, which is information indicating that the user's payment is paid, to the fluoroscopic apparatus 10 when the user's payment is made by the date of payment.

Then, the controller 12d as the fluoroscopy prohibition unit 43 performs a control to prohibit X-ray fluoroscopy by the fluoroscopic apparatus 10 when determining that the unpaid information 52 has been received from the server apparatus 20. Alternatively, the controller 12d as the fluoroscopy prohibition unit 43 performs a control to prohibit X-ray fluoroscopy by the fluoroscopic apparatus 10 when determining that the paid information 53 has not been received from the server apparatus 20. Furthermore, the controller 12d as the fluoroscopy prohibition unit 43 does not perform a control to prohibit X-ray fluoroscopy by the fluoroscopic apparatus 10 when determining that the paid information 53 has been received from the server apparatus 20.

Advantages of First Embodiment

In the first embodiment, the following advantages are obtained.

In the first embodiment, as described above, the X-ray tube billing system 100 includes the billing amount calculator 73 that calculates the billing amount related to the use of the X-ray tube 200 based on the length of time during which X-ray fluoroscopy has been performed, which is detected by the fluoroscopy time detector 41. Accordingly, it is possible to charge based on the length of time during which X-ray fluoroscopy has been performed, and thus it is possible to provide the X-ray tube billing system 100 capable of charging fairly even when the time taken for one-time X-ray fluoroscopy differs depending on the user unlike a case of charging based on the number of times of X-ray fluoroscopy when the fluoroscopic apparatus 10 for non-destructive inspection is used. That is, unlike a medical digital X-ray imaging apparatus as described in Patent Document 1, in the fluoroscopic apparatus 10 for non-destructive inspection that performs X-ray fluoroscopy on the subject 300, the time taken for one-time X-ray imaging (X-ray fluoroscopy) often differs depending on the user. In other words, in the fluoroscopic apparatus 10, which is a non-destructive inspection apparatus, the required fluoroscopy time greatly varies depending on the external shape and internal structure of an observation material, which is the subject 300. However, in the first embodiment, it is possible to charge based on the length of time during which X-ray fluoroscopy has been performed, and thus the charge can be made fairly.

In the first embodiment, as described above, the X-ray tube billing system 100 includes the fluoroscopy time integrator 74 that adds up the length of time during which X-ray fluoroscopy has been performed during the predetermined period. Furthermore, the billing amount calculator 73 is configured to calculate the billing amount for the predetermined period based on the length of time during which the X-ray fluoroscopy has been performed during the predetermined period added up by the fluoroscopy time integrator 74. Accordingly, the billing amount can be easily calculated for each predetermined period by the billing amount calculator 73, and thus it is possible to easily charge the user for the billing amount for each predetermined period.

In the first embodiment, as described above, the fluoroscopy time integrator 74 is configured to add up the length of time during which X-ray fluoroscopy has been performed during the predetermined period in association with the apparatus ID 31, which is the identification information of the fluoroscopic apparatus 10. Furthermore, the billing amount calculator 73 is configured to calculate the billing amount of the specific fluoroscopic apparatus 10 for the predetermined period based on the length of time during which X-ray fluoroscopy has been performed during the predetermined period added up by the fluoroscopy time integrator 74. Accordingly, the billing amount for the predetermined period can be easily calculated for each fluoroscopic apparatus 10 by the billing amount calculator 73, and thus it is possible to easily charge the billing amount of each of the plurality of fluoroscopic apparatuses 10 for the predetermined period.

In the first embodiment, as described above, the fluoroscopy time integrator 74 is configured to add up the length of time during which X-ray fluoroscopy has been performed from the start of use of the specific X-ray tube 200 to the present time in association with the X-ray tube ID 32, which is the identification information of the X-ray tube 200. Accordingly, the total usage time of the X-ray tube 200 can be confirmed, and thus the life of the X-ray tube 200 can be predicted to predict the replacement time of the X-ray tube 200. When the total usage time of a plurality of X-ray tubes 200, which are rental items, is managed in the server apparatus 20 as in the first embodiment, the replacement time of each of the plurality of X-ray tubes 200 is predicted such that it is possible to grasp how many spare X-ray tubes 200, which are rental items, should be possessed. Thus, it is possible to significantly reduce or prevent a failure in quick replacement of the X-ray tube 200, which is a rental item, due to not having a spare X-ray tube 200 while excessive possession of spare X-ray tubes 200 is significantly reduced or prevented.

In the first embodiment, as described above, the X-ray tube billing system 100 includes the controller 12d that controls the display 80 to display the billing amount calculated by the billing amount calculator 73. Accordingly, the user can visually easily and reliably confirm the billing amount to be charged.

In the first embodiment, as described above, the X-ray tube billing system 100 includes the fluoroscopic apparatus 10 and the server apparatus 20. Furthermore, the fluoroscopic apparatus 10 includes the X-ray tube 200 for X-ray fluoroscopy on the subject 300 and the fluoroscopy time transmitter 42 that transmits the fluoroscopy time information 51, which is the information on the length of time during which X-ray fluoroscopy has been performed, to the server apparatus 20. Moreover, the server apparatus 20 includes the fluoroscopy time receiver 71 that receives the fluoroscopy time information 51, which is the information on the length of time during which X-ray fluoroscopy has been performed, and the billing amount calculator 73 that calculates the billing amount based on the length of time during which X-ray fluoroscopy has been performed. Accordingly, the billing amount can be calculated in the server apparatus 20, and thus unlike a case in which the billing amount is calculated in the fluoroscopic apparatus 10, the billing amount can be calculated while an increase in the processing load on the fluoroscopic apparatus 10 is significantly reduced or prevented.

In the first embodiment, as described above, the fluoroscopy time transmitter 42 is configured to transmit, to the server apparatus 20, the fluoroscopy time information 51, which is the information on the length of time during which X-ray fluoroscopy has been performed, in association with the Apparatus ID 31, which is the identification information of the fluoroscopic apparatus 10, and the X-ray tube ID 32, which is the identification information of the X-ray tube 200. Accordingly, it is possible to identify which fluoroscopic apparatus 10 and which X-ray tube 200 the information on the length of time during which X-ray fluoroscopy has been performed belongs to in the server apparatus 20, and thus the information on the length of time during which X-ray fluoroscopy has been performed can be easily managed in the server apparatus 20.

In the first embodiment, as described above, the X-ray tube billing system 100 includes the fluoroscopy prohibition unit 43 that performs a control to prohibit X-ray fluoroscopy when the fluoroscopy time transmitter 42 is unable to transmit the fluoroscopy time when the X-ray fluoroscopy is performed. Accordingly, when the fluoroscopy time transmitter 42 of the fluoroscopic apparatus 10 is unable to transmit the fluoroscopy time, it is possible to prevent the fluoroscopic apparatus 10 from performing X-ray fluoroscopy, and thus it is possible to prevent the fluoroscopy time from not being transmitted despite performing X-ray fluoroscopy. Consequently, it is possible to significantly reduce or prevent a failure in accurate calculation of the billing amount in the server apparatus 20 due to the fluoroscopy time not being transmitted.

In the first embodiment, as described above, the X-ray tube billing system 100 includes the fluoroscopy prohibition unit 43 that performs a control to prohibit X-ray fluoroscopy when the user's payment of the billing amount is not made by the date of payment. Accordingly, when the user's payment of the billing amount is not made by the date of payment and is delayed, it is possible to prevent X-ray fluoroscopy by the fluoroscopic apparatus 10, and thus it is possible to prevent the fluoroscopic apparatus 10 from being used by the user although the user's payment of the billing amount is delayed.

Second Embodiment

Figure 10:
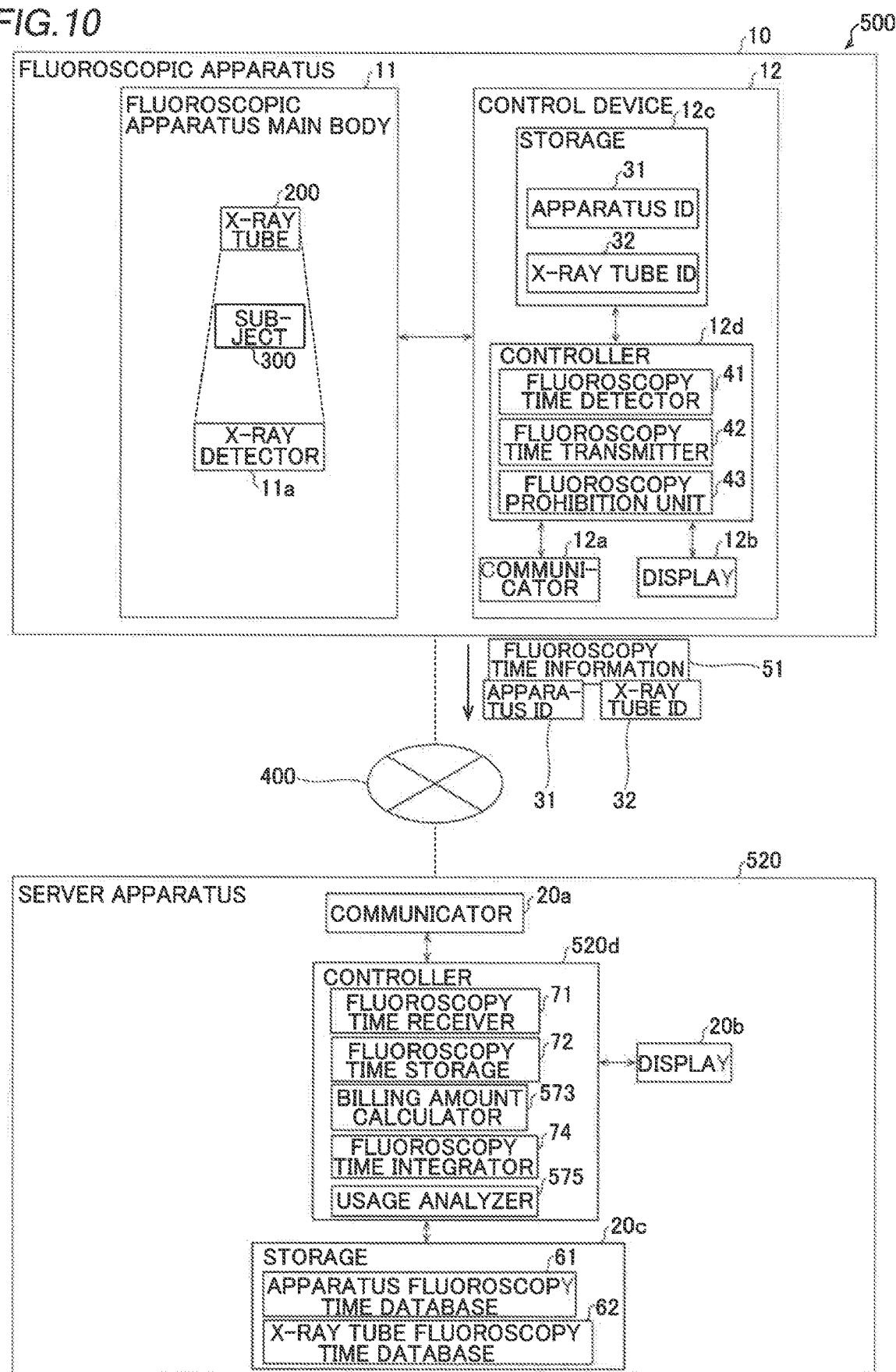
FIG. 10 is a schematic view showing the overall configuration of an X-ray tube billing system according to a second embodiment of the present invention.

A second embodiment is now described with reference to FIGS. 10 to 14. The same or similar configurations as those of the first embodiment are denoted by the same reference numerals in the figures, and description thereof is omitted.
Configuration of X-Ray Tube Billing System As shown in FIG. 10, an X-ray tube billing system 500 according to the second embodiment includes a server apparatus 520 instead of the server apparatus 20 according to the first embodiment.

The server apparatus 520 includes a controller 520d instead of the controller 20d according to the first embodiment. The controller 520d is a control circuit that includes a processor such as a CPU and a memory for storing information, for example, and controls the operation of each portion of the server apparatus 520. The controller 520d functions as a fluoroscopy time receiver 71, a fluoroscopy time storage 72, a billing amount calculator 573, a fluoroscopy time integrator 74, and a usage analyzer 575 by executing various programs (software). That is, the fluoroscopy time receiver 71, the fluoroscopy time storage 72, the billing amount calculator 573, the fluoroscopy time integrator 74, and the usage analyzer 575 are illustrated as software functional blocks. Note that they are not limited to these, but they may be configured in whole or in part by dedicated hardware circuits. Furthermore, the fluoroscopy time receiver 71, the fluoroscopy time storage 72, and the fluoroscopy time integrator 74 have the same configurations as those of the first embodiment, and thus description thereof is omitted.

Figure 11:
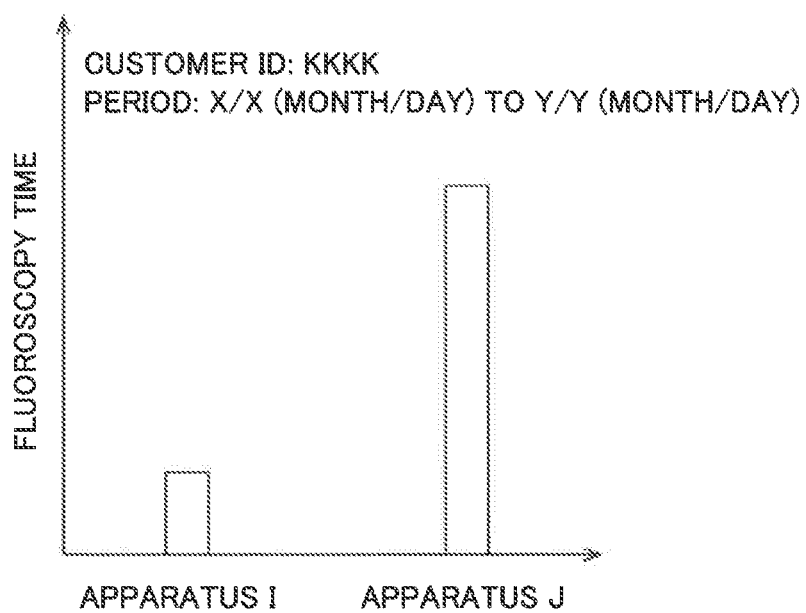
FIG. 11 is a first graph illustrating leveling of the usages of a plurality of fluoroscopic apparatuses of the X-ray tube billing system according to the second embodiment of the present invention.

As shown in FIG. 11, some users may own a plurality of fluoroscopic apparatuses 10. Furthermore, the plurality of fluoroscopic apparatuses 10 owned by the user may include a fluoroscopic apparatus 10 having a high operating rate and an idle fluoroscopic apparatus 10 having a low operating rate. In this case, in the fluoroscopic apparatus 10 having a high operating rate, the number of consumables increases, and thus the maintenance cost increases. Even in the fluoroscopic apparatus 10 having a low operating rate, some components are fragile when used occasionally, and thus the maintenance cost increases. Therefore, from the viewpoint of reducing the maintenance cost, it is desirable to level the usages of the plurality of fluoroscopic apparatuses 10.

Therefore, in the second embodiment, the controller 520d as the usage analyzer 575 analyzes the past usages of the plurality of fluoroscopic apparatuses 10 based on the lengths of time during which the plurality of fluoroscopic apparatuses 10 have performed X-ray fluoroscopy, as shown in FIG. 11. Specifically, the controller 520d as the usage analyzer 575 analyzes a status of leveling of the usages of the plurality of fluoroscopic apparatuses 10 based on the lengths of time during which the plurality of fluoroscopic apparatuses 10 have performed X-ray fluoroscopy. Although the usages of two fluoroscopic apparatuses 10 (apparatuses I and J) are shown as an example in FIG. 11, the number of fluoroscopic apparatuses 10, the usages of which are analyzed, may be three or more.

The controller 520d as the usage analyzer 575 acquires, from a storage 20c, the lengths of time during which a plurality of fluoroscopic apparatuses 10 owned by a specific user (in FIG. 11, a user whose customer ID 33 is "KKKK") have performed X-ray fluoroscopy during a predetermined period. Furthermore, the controller 520d as the usage analyzer 575 analyzes the status of leveling of the usages of the plurality of fluoroscopic apparatuses 10 owned by the specific user for the predetermined period based on the acquired lengths of time during which the plurality of fluoroscopic apparatuses 10 have performed X-ray fluoroscopy during the predetermined period. The predetermined period may be any period, and may be a period of one month or three months, for example.

Figure 12:
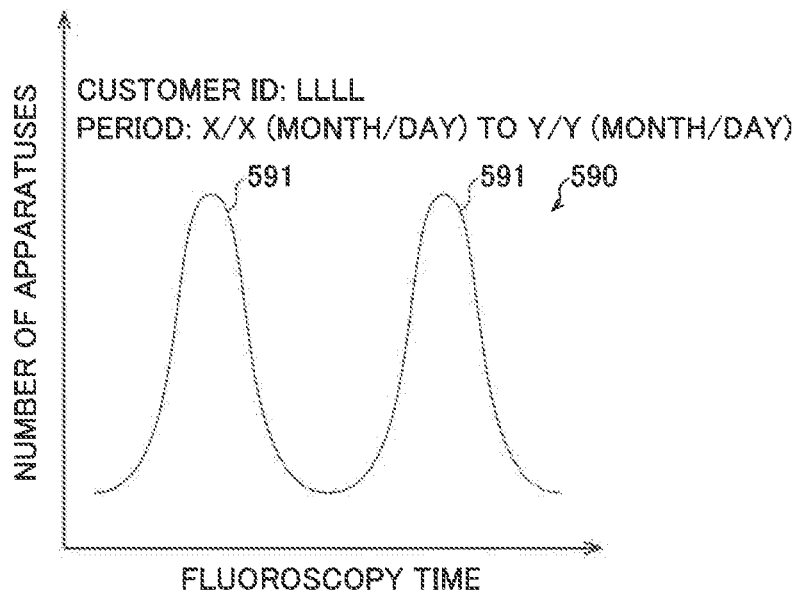
FIG. 12 is a second graph illustrating leveling of the usages of the plurality of fluoroscopic apparatuses of the X-ray tube billing system according to the second embodiment of the present invention.

The controller 520d as the usage analyzer 575 detects that the usages of the plurality of fluoroscopic apparatuses are not leveled when the usages of the plurality of fluoroscopic apparatuses 10 are not leveled (i.e., the case as shown in FIG. 11). The detection that the usages of the plurality of fluoroscopic apparatuses 10 are not leveled may be performed in any manner, and the detection may be performed by comparing the lengths of time during which the plurality of fluoroscopic apparatuses 10 have performed X-ray fluoroscopy during the predetermined period with each other, for example. For example, as shown in FIG. 12, when the horizontal axis represents the length of time during which X-ray fluoroscopy has been performed during the predetermined period and the vertical axis represents the number of fluoroscopic apparatuses 10, a distribution 590 showing the correlation between the length of time during which X-ray fluoroscopy has been performed during the predetermined period and the number of fluoroscopic apparatuses 10 is obtained. When the operating rates of the plurality of fluoroscopic apparatuses 10 vary, the distribution 590 includes a plurality of peaks 591, and thus the degree of separation between the peaks 591 is acquired such that it is possible to detect that the usages of the plurality of fluoroscopic apparatuses 10 are not leveled based on the degree of separation between the peaks 591.

Figure 13:
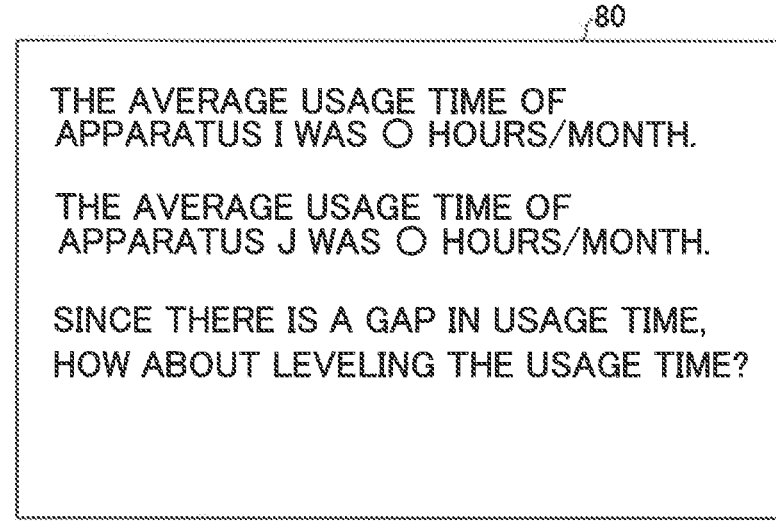
FIG. 13 is a schematic view illustrating display of a proposal for leveling the usage of the X-ray tube billing system according to the second embodiment of the present invention.

When it is detected that the usages of the plurality of fluoroscopic apparatuses 10 are not leveled, it is possible to notify the user of information prompting leveling of the usages of the plurality of fluoroscopic apparatuses 10. The user may be notified of the information promoting the leveling in any manner, and the user may be notified via a network 400, by telephone, or in writing, for example. When the user is notified via the network 400, the user may be notified by displaying the information promoting the leveling on a display 80, as shown in FIG. 13, for example. That is, the user may be notified of the information prompting the leveling by displaying the information prompting the leveling on a display 12b of the fluoroscopic apparatus 10 used by the user who needs to confirm the information prompting the leveling or a display of a terminal (such as a personal computer or a mobile terminal) used by the user who needs to confirm the information prompting the leveling.

The controller 520d as the billing amount calculator 573 has the same configuration as the billing amount calculator 73 according to the first embodiment. In addition, in the second embodiment, the controller 520d as the billing amount calculator 573 calculates the expected future billing amount based on the length of time during which X-ray fluoroscopy has been performed. That is, the controller 520d as the billing amount calculator 573 calculates the expected future billing amount based on the usage record of an X-ray tube 200. The expected future billing amount may be the billing amount for the next month, the billing amount for the user's next budget setting period (such as the next half year), or the like.

The controller 520*d* as the billing amount calculator 573 calculates the expected future billing amount of a specific fluoroscopic apparatus 10 owned by the user, for example. Furthermore, the controller 520*d* as the billing amount calculator 573 calculates the expected future billing amounts of the plurality of fluoroscopic apparatuses 10 owned by the user, for example.

Figure 14:
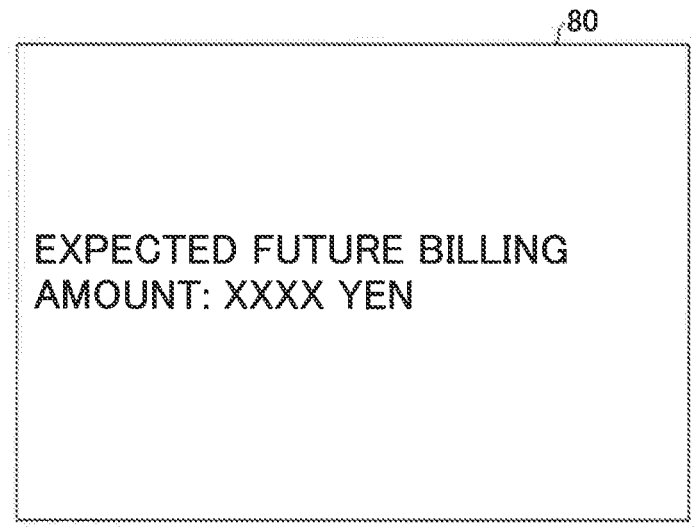
FIG. 14 is a schematic view illustrating display of the expected future billing amount of the X-ray tube billing system according to the second embodiment of the present invention.

When the expected future billing amount is calculated, the user can be notified of the calculated expected future billing amount. The user may be notified of the expected future billing amount in any manner, and may be notified via the network 400 or in writing, for example. When the user is notified via the network 400, the user may be notified by displaying the expected future billing amount on the display 80, as shown in FIG. 14, for example. That is, the user may be notified of the expected future billing amount by displaying the expected future billing amount on the display 12*b* of the fluoroscopic apparatus 10 used by the user who needs to confirm the expected future billing amount or the display of the terminal (such as the personal computer or the mobile terminal) used by the user who needs to confirm the expected future billing amount.

In the above description, it is determined whether or not the usages are leveled in the plurality of fluoroscopic apparatuses 10 owned by one specific customer, but the present invention is not limited to this. In the fluoroscopic apparatuses 10 owned by a plurality of customers, the usages (operating rates) may be compared to determine the degree of leveling for each customer, and a customer of the fluoroscopic apparatus 10 having a relatively low operating rate may be notified.

Advantages of Second Embodiment

In the second embodiment, the following advantages are obtained.

In the second embodiment, as described above, the X-ray tube billing system 500 includes the billing amount calculator 573 that calculates the billing amount related to the use of the X-ray tube 200 based on the length of time during which X-ray fluoroscopy has been performed, which is detected by a fluoroscopy time detector 41. Accordingly, similarly to the first embodiment, it is possible to provide the X-ray tube billing system 500 capable of charging fairly even when the time taken for one-time X-ray fluoroscopy differs depending on the user unlike a case of charging based on the number of times of X-ray fluoroscopy when the fluoroscopic apparatus 10 for non-destructive inspection is used.

In the second embodiment, as described above, the X-ray tube billing system 500 includes the usage analyzer 575 that analyzes the past usages of the plurality of fluoroscopic apparatuses 10 based on the lengths of time during which the plurality of fluoroscopic apparatuses 10 have performed X-ray fluoroscopy. Accordingly, for example, an operation proposal for leveling the usages of the plurality of fluoroscopic apparatuses 10 can be made to the user (the owner of the fluoroscopic apparatuses 10) based on the analysis results of the past usages of the plurality of fluoroscopic apparatuses 10. Consequently, the user can effectively use the plurality of fluoroscopic apparatus 10*s* owned by the user. Furthermore, it is possible to significantly reduce or prevent an increase in the maintenance cost of the fluoroscopic apparatuses 10 due to the usages of the plurality of fluoroscopic apparatuses 10 not being leveled.

In the second embodiment, as described above, the usage analyzer 575 is configured to analyze the status of leveling of the usages of the plurality of fluoroscopic apparatuses 10 based on the lengths of time during which the plurality of fluoroscopic apparatuses 10 have performed X-ray fluoroscopy. Accordingly, it is possible to easily detect that the usages of the plurality of fluoroscopic apparatuses 10 are not leveled, and thus an operation proposal for leveling the usages of the plurality of fluoroscopic apparatuses 10 can be easily made to the user.

In the second embodiment, as described above, the billing amount calculator 573 is configured to calculate the expected future billing amount based on the length of time during which X-ray fluoroscopy has been performed. Accordingly, the user can grasp the expected future billing amount, and thus the budget can be easily developed. Consequently, the convenience of the X-ray tube billing system 500 can be improved as compared with a case in which the X-ray tube billing system calculates only the actual billing amount.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the fluoroscopic apparatus includes the fluoroscopy time detector, and the server apparatus includes the billing amount calculator has been shown in each of the aforementioned first and second embodiments, the present invention is not limited to this. In the present invention, as long as the billing amount can be calculated based on the length of time during which X-ray fluoroscopy has been performed, the server apparatus may include the fluoroscopy time detector and the billing amount calculator, or the fluoroscopic apparatus may include the fluoroscopy time detector and the billing amount calculator. When the server apparatus includes the fluoroscopy time detector, the fluoroscopy time detector of the server apparatus may detect the length of time during which X-ray fluoroscopy has been performed in the fluoroscopic apparatus based on information at the start of the X-ray fluoroscopy and information at the end of the X-ray fluoroscopy received from the fluoroscopic apparatus. When the fluoroscopic apparatus includes the billing amount calculator, the fluoroscopic apparatus may transmit the billing amount calculated by the billing amount calculator of the fluoroscopic apparatus to the server apparatus and store it in the server apparatus.

While the example in which the information on the length of time during which X-ray fluoroscopy has been performed is transmitted in association with the apparatus ID (the identification information of the fluoroscopic apparatus) and the X-ray tube ID (the identification information of the X-ray tube) from the fluoroscopic apparatus to the server apparatus has been shown in each of the aforementioned first and second embodiments, the present invention is not limited to this. In the present invention, the information on the length of time during which X-ray fluoroscopy has been performed may not be transmitted in association with the identification information of the fluoroscopic apparatus and the identification information of the X-ray tube from the fluoroscopic apparatus to the server apparatus.

For example, the information on the length of time during which X-ray fluoroscopy has been performed may be transmitted in association only with the identification information of the fluoroscopic apparatus from the fluoroscopic apparatus to the server apparatus. In this case, the X-ray tube billing system may be configured not to use the identification information of the X-ray tube at all, or the server apparatus of the X-ray tube billing system may be configured to have information that associates the identification information of the fluoroscopic apparatus with the identification information of the X-ray tube. Thus, the X-ray tube used for X-ray fluoroscopy can be identified in the server apparatus simply by transmitting the identification information of the fluoroscopic apparatus from the fluoroscopic apparatus to the server apparatus.

For example, the information on the length of time during which X-ray fluoroscopy has been performed may be transmitted in association only with the identification information of the X-ray tube from the fluoroscopic apparatus to the server apparatus. In this case, the X-ray tube billing system may be configured not to use the identification information of the fluoroscopic apparatus at all, or the server apparatus of the X-ray tube billing system may be configured to have the information that associates the identification information of the fluoroscopic apparatus with the identification information of the X-ray tube. Thus, the fluoroscopic apparatus that has performed X-ray fluoroscopy can be identified in the server apparatus simply by transmitting the identification information of the X-ray tube from the fluoroscopic apparatus to the server apparatus.

For example, the information on the length of time during which X-ray fluoroscopy has been performed may be transmitted in association with customer identification information (customer ID) from the fluoroscopic apparatus to the server apparatus. In this case, the X-ray tube billing system may be configured not to use the identification information of the fluoroscopic apparatus and the identification information of the X-ray tube at all, or the server apparatus of the X-ray tube billing system may be configured to have information that associates the customer identification information with the identification information of the fluoroscopic apparatus and the identification information of the X-ray tube. Thus, the fluoroscopic apparatus and the X-ray tube used for X-ray fluoroscopy can be identified in the server apparatus simply by transmitting the customer identification information from the fluoroscopic apparatus to the server apparatus.

While the example in which the fluoroscopic apparatus includes the fluoroscopy prohibition unit has been shown in each of the aforementioned first and second embodiments, the present invention is not limited to this. In the present invention, the fluoroscopic apparatus may not include the fluoroscopy prohibition unit.

While the example in which the X-ray tube billing system includes the usage analyzer has been shown in the aforementioned second embodiment, the present invention is not limited to this. In the present invention, the X-ray tube billing system may not include the usage analyzer.

Aspects

It will be appreciated by those skilled in the art that the exemplary embodiments described above are specific examples of the following aspects.

(Item 1)

An X-ray tube billing system for a fluoroscopic apparatus for non-destructive inspection configured to perform X-ray fluoroscopy on a subject using an X-ray tube, the X-ray tube billing system comprising:
   a fluoroscopy time detector configured to detect a length of time during which the X-ray fluoroscopy has been performed using the X-ray tube; and
   a billing amount calculator configured to calculate a billing amount related to use of the X-ray tube based on the length of time during which the X-ray fluoroscopy has been performed, which is detected by the fluoroscopy time detector.

(Item 2)

The X-ray tube billing system according to item 1, further comprising:
   a fluoroscopy time integrator configured to add up a length of time during which the X-ray fluoroscopy has been performed during a first predetermined period; wherein
   the billing amount calculator is configured to calculate the billing amount for the first predetermined period based on the length of time during which the X-ray fluoroscopy has been performed during the first predetermined period added up by the fluoroscopy time integrator.

(Item 3)

The X-ray tube billing system according to item 2, wherein
   the fluoroscopy time integrator is configured to add up the length of time during which the X-ray fluoroscopy has been performed during the first predetermined period in association with identification information of the fluoroscopic apparatus; and
   the billing amount calculator is configured to calculate the billing amount of a specific fluoroscopic apparatus for the first predetermined period based on the length of time during which the X-ray fluoroscopy has been performed during the first predetermined period added up by the fluoroscopy time integrator.

(Item 4)

The X-ray tube billing system according to any one of items 1 to 3, comprising:
   a fluoroscopy time integrator configured to add up a length of time during which the X-ray fluoroscopy has been performed from a start of use of a specific X-ray tube to a present time in association with identification information of the X-ray tube.

(Item 5)

The X-ray tube billing system according to any one of items 1 to 4, further comprising:
   a display controller configured to control a display to display the billing amount calculated by the billing amount calculator.

(Item 6)

The X-ray tube billing system according to any one of items 1 to 5, comprising:
   the fluoroscopic apparatus and a server apparatus; wherein
   the fluoroscopic apparatus includes:
      the X-ray tube for the X-ray fluoroscopy on the subject; and
      a fluoroscopy time transmitter configured to transmit, to the server apparatus, information on the length of time during which the X-ray fluoroscopy has been performed; and the server apparatus includes:
a fluoroscopy time receiver configured to receive the information on the length of time during which the X-ray fluoroscopy has been performed; and
the billing amount calculator configured to calculate the billing amount based on the length of time during which the X-ray fluoroscopy has been performed.

(Item 7)

The X-ray tube billing system according to item 6, wherein the fluoroscopy time transmitter is configured to transmit, to the server apparatus, the information on the length of time during which the X-ray fluoroscopy has been performed in association with identification information of the fluoroscopic apparatus and identification information of the X-ray tube.

(Item 8)

The X-ray tube billing system according to item 7, wherein
the server apparatus is configured to:
determine whether or not the X-ray tube is unused for a second predetermined period based on the information on the length of time during which the X-ray fluoroscopy has been performed, which is associated with the identification information of the X-ray tube; and
transmit, to the fluoroscopic apparatus, information prompting use of the X-ray tube when determining that the X-ray tube is unused for a second predetermined period.

(Item 9)

The X-ray tube billing system according to item 7 or 8, wherein the server apparatus includes a fluoroscopy time integrator configured to add up a length of time during which the X-ray fluoroscopy has been performed from a start of use of a specific X-ray tube to a present time based on the information on the length of time during which the X-ray fluoroscopy has been performed, which is associated with the identification information of the X-ray tube.

(Item 10)

The X-ray tube billing system according to any one of items 7 to 9, wherein the billing amount calculator is configured to calculate the billing amount based on the length of time during which the X-ray fluoroscopy has been performed, using a different charge system preset for at least one of the identification information of the fluoroscopic apparatus or the identification information of the X-ray tube.

(Item 11)

The X-ray tube billing system according to any one of items 7 to 10, wherein
the fluoroscopy time transmitter is configured to transmit, to the server apparatus, the information on the length of time during which the X-ray fluoroscopy has been performed in association with at least one of a fluoroscopic mode or a fluoroscopic condition used for the X-ray fluoroscopy; and
the billing amount calculator is configured to calculate the billing amount based on the length of time during which the X-ray fluoroscopy has been performed, using a different charge system preset for at least one of the fluoroscopic mode or the fluoroscopic condition.

(Item 12)

The X-ray tube billing system according to any one of items 6 to 11, further comprising:
a fluoroscopy prohibition unit configured to perform a control to prohibit the X-ray fluoroscopy when the fluoroscopy time transmitter is unable to transmit a fluoroscopy time when the X-ray fluoroscopy is performed.

(Item 13)

The X-ray tube billing system according to any one of items 6 to 12, further comprising:
a fluoroscopy prohibition unit configured to perform a control to prohibit the X-ray fluoroscopy when user's payment of the billing amount is not made by a date of payment.

(Item 14)

The X-ray tube billing system according to any one of items 1 to 13, further comprising:
a usage analyzer configured to analyze past usages of a plurality of fluoroscopic apparatuses based on lengths of time during which the plurality of fluoroscopic apparatuses have performed the X-ray fluoroscopy.

(Item 15)

The X-ray tube billing system according to item 14, wherein the usage analyzer is configured to analyze a status of leveling of usages of the plurality of fluoroscopic apparatuses based on the lengths of time during which the plurality of fluoroscopic apparatuses have performed the X-ray fluoroscopy.

(Item 16)

The X-ray tube billing system according to any one of items 1 to 15, wherein the billing amount calculator is configured to calculate an expected future billing amount based on the length of time during which the X-ray fluoroscopy has been performed.

DESCRIPTION OF REFERENCE NUMERALS

10: fluoroscopic apparatus
12d: controller (display controller)
20, 520: server apparatus
20d: controller (display controller)
31: apparatus ID (identification information of the fluoroscopic apparatus)
32: X-ray tube ID (identification information of the X-ray tube)
41: fluoroscopy time detector
42: fluoroscopy time transmitter
43: fluoroscopy prohibition unit
51: information on the length of time during which X-ray fluoroscopy has been performed
71: fluoroscopy time receiver
73, 573: billing amount calculator
74: fluoroscopy time integrator
80: display
100, 500: X-ray tube billing system
200: X-ray tube
300: subject
575: usage analyzer

The invention claimed is:

1. An X-ray tube billing system for a fluoroscopic apparatus for non-destructive inspection configured to perform X-ray fluoroscopy on a subject using an X-ray tube, the X-ray tube billing system comprising:
a fluoroscopy time detector configured to detect a length of time during which the X-ray fluoroscopy, which is moving image capturing to continuously image the subject, has been performed using the X-ray tube; and
a billing amount calculator configured to calculate a billing amount related to use of the X-ray tube based on the length of time during which the X-ray fluoroscopy has been performed, which is detected by the fluoroscopy time detector.

2. The X-ray tube billing system according to claim 1, further comprising:
a fluoroscopy time integrator configured to add up a length of time during which the X-ray fluoroscopy has been performed during a first predetermined period; wherein
the billing amount calculator is configured to calculate the billing amount for the first predetermined period based on the length of time during which the X-ray fluoroscopy has been performed during the first predetermined period added up by the fluoroscopy time integrator.

3. The X-ray tube billing system according to claim 2, wherein
the fluoroscopy time integrator is configured to add up the length of time during which the X-ray fluoroscopy has been performed during the first predetermined period in association with identification information of the fluoroscopic apparatus; and
the billing amount calculator is configured to calculate the billing amount of a specific fluoroscopic apparatus for the first predetermined period based on the length of time during which the X-ray fluoroscopy has been performed during the first predetermined period added up by the fluoroscopy time integrator.

4. The X-ray tube billing system according to claim 1, comprising:
a fluoroscopy time integrator configured to add up a length of time during which the X-ray fluoroscopy has been performed from a start of use of a specific X-ray tube to a present time in association with identification information of the X-ray tube.

5. The X-ray tube billing system according to claim 1, further comprising:
a display controller configured to control a display to display the billing amount calculated by the billing amount calculator.

6. The X-ray tube billing system according to claim 1, comprising:
the fluoroscopic apparatus and a server apparatus; wherein
the fluoroscopic apparatus includes:
the X-ray tube for the X-ray fluoroscopy on the subject; and
a fluoroscopy time transmitter configured to transmit, to the server apparatus, information on the length of time during which the X-ray fluoroscopy has been performed; and
the server apparatus includes:
a fluoroscopy time receiver configured to receive the information on the length of time during which the X-ray fluoroscopy has been performed; and
the billing amount calculator configured to calculate the billing amount based on the length of time during which the X-ray fluoroscopy has been performed.

7. The X-ray tube billing system according to claim 6, wherein the fluoroscopy time transmitter is configured to transmit, to the server apparatus, the information on the length of time during which the X-ray fluoroscopy has been performed in association with identification information of the fluoroscopic apparatus and identification information of the X-ray tube.

8. The X-ray tube billing system according to claim 7, wherein
the server apparatus is configured to:
determine whether or not the X-ray tube is unused for a second predetermined period based on the information on the length of time during which the X-ray fluoroscopy has been performed, which is associated with the identification information of the X-ray tube; and
transmit, to the fluoroscopic apparatus, information prompting use of the X-ray tube when determining that the X-ray tube is unused for the second predetermined period.

9. The X-ray tube billing system according to claim 7, wherein the server apparatus includes a fluoroscopy time integrator configured to add up a length of time during which the X-ray fluoroscopy has been performed from a start of use of a specific X-ray tube to a present time based on the information on the length of time during which the X-ray fluoroscopy has been performed, which is associated with the identification information of the X-ray tube.

10. The X-ray tube billing system according to claim 7, wherein the billing amount calculator is configured to calculate the billing amount based on the length of time during which the X-ray fluoroscopy has been performed, using a different charge system preset for at least one of the identification information of the fluoroscopic apparatus or the identification information of the X-ray tube.

11. The X-ray tube billing system according to claim 7, wherein
the fluoroscopy time transmitter is configured to transmit, to the server apparatus, the information on the length of time during which the X-ray fluoroscopy has been performed in association with at least one of a fluoroscopic mode or a fluoroscopic condition used for the X-ray fluoroscopy; and
the billing amount calculator is configured to calculate the billing amount based on the length of time during which the X-ray fluoroscopy has been performed, using a different charge system preset for at least one of the fluoroscopic mode or the fluoroscopic condition.

12. The X-ray tube billing system according to claim 6, further comprising:
a fluoroscopy prohibition unit configured to perform a control to prohibit the X-ray fluoroscopy when the fluoroscopy time transmitter is unable to transmit a fluoroscopy time when the X-ray fluoroscopy is performed.

13. The X-ray tube billing system according to claim 6, further comprising:
a fluoroscopy prohibition unit configured to perform a control to prohibit the X-ray fluoroscopy when user's payment of the billing amount is not made by a date of payment.

14. The X-ray tube billing system according to claim 1, further comprising:
a usage analyzer configured to analyze past usages of a plurality of fluoroscopic apparatuses based on lengths of time during which the plurality of fluoroscopic apparatuses have performed the X-ray fluoroscopy.

15. The X-ray tube billing system according to claim 14, wherein the usage analyzer is configured to analyze a status of leveling of usages of the plurality of fluoroscopic apparatuses based on the lengths of time during which the plurality of fluoroscopic apparatuses have performed the X-ray fluoroscopy.

16. The X-ray tube billing system according to claim 1, wherein the billing amount calculator is configured to calculate an expected future billing amount based on the length of time during which the X-ray fluoroscopy has been performed.

17. A server apparatus connectable to a fluoroscopic apparatus, the server apparatus comprising:
- a fluoroscopy time receiver configured to receive, from the fluoroscopic apparatus, information on a length of time during which the fluoroscopic apparatus has performed X-ray fluoroscopy, which is moving image capturing to continuously image a subject; and
- a billing amount calculator configured to calculate a billing amount related to use of an X-ray tube based on the length of time during which the fluoroscopic apparatus has performed the X-ray fluoroscopy.

18. A fluoroscopic apparatus connectable to a server apparatus, the fluoroscopic apparatus comprising:
- a connector connected to the server apparatus including a billing amount calculator configured to calculate a billing amount related to use of an X-ray tube based on a length of time during which X-ray fluoroscopy has been performed;
- the X-ray tube for the X-ray fluoroscopy on a subject; and
- a fluoroscopy time transmitter configured to transmit, to the server apparatus, information on the length of time during which the X-ray fluoroscopy, which is moving image capturing to continuously image the subject, has been performed.

19. An X-ray tube billing method for a fluoroscopic apparatus for non-destructive inspection configured to perform X-ray fluoroscopy on a subject using an X-ray tube, the X-ray tube billing method comprising:
- receiving a length of time during which the X-ray fluoroscopy, which is moving image capturing to continuously image the subject, has been performed using the X-ray tube; and
- calculating a billing amount related to use of the X-ray tube based on the received length of time during which the X-ray fluoroscopy has been performed.

* * * * *